US007415928B2

(12) United States Patent
Stiel

(10) Patent No.: US 7,415,928 B2
(45) Date of Patent: Aug. 26, 2008

(54) PRINTING MACHINES WITH AT LEAST ONE COLOR SUPPORT

(75) Inventor: Jürgen Alfred Stiel, Thüngen (DE)

(73) Assignee: Koenig & Bauer Aktiengesellschaft, Wurzburg (DE)

( * ) Notice: Subject to any disclaimer, the term of this patent is extended or adjusted under 35 U.S.C. 154(b) by 496 days.

(21) Appl. No.: 10/535,656

(22) PCT Filed: Sep. 3, 2003

(86) PCT No.: PCT/DE03/02907

§ 371 (c)(1),
(2), (4) Date: May 19, 2005

(87) PCT Pub. No.: WO2004/052648

PCT Pub. Date: Jun. 24, 2004

(65) Prior Publication Data

US 2006/0096475 A1 May 11, 2006

(30) Foreign Application Priority Data

Dec. 6, 2002 (DE) ................................ 102 57 132

(51) Int. Cl.
*A01H 5/02* (2006.01)
*B41F 31/00* (2006.01)
*G03C 8/00* (2006.01)
*B41J 2/47* (2006.01)

(52) U.S. Cl. ........................ 101/171; 101/491; 347/232; 430/201

(58) Field of Classification Search ................. 101/183, 101/181, 211, 171, 491; 430/200, 201; 347/103, 347/232
See application file for complete search history.

(56) References Cited

U.S. PATENT DOCUMENTS

| | | | | |
|---|---|---|---|---|
| 2,616,961 | A | 11/1952 | Groak | |
| 3,745,586 | A * | 7/1973 | Braudy | 347/253 |
| 3,798,365 | A * | 3/1974 | Browning et al. | 358/296 |
| 5,021,808 | A | 6/1991 | Kohyama | |
| 5,157,412 | A * | 10/1992 | Kleinschmidt et al. | 347/232 |
| 6,056,388 | A * | 5/2000 | Maximovsky et al. | 347/51 |
| 6,330,857 | B1 | 12/2001 | Maximovsky et al. | |
| 6,386,696 | B1 | 5/2002 | Rodi et al. | |
| 6,651,560 | B2 * | 11/2003 | Neuhaus | 101/401.1 |
| 6,857,368 | B2 * | 2/2005 | Pitz | 101/484 |
| 2003/0156178 | A1 | 8/2003 | Lehmann | |

FOREIGN PATENT DOCUMENTS

| | | |
|---|---|---|
| DE | 37 02 643 A1 | 8/1987 |
| DE | 195 30 284 A1 | 2/1997 |

(Continued)

*Primary Examiner*—Anthony H. Nguyen
*Assistant Examiner*—Leo T Hinze
(74) *Attorney, Agent, or Firm*—Jones, Yullar & Cooper, P.C.

(57) ABSTRACT

A printing press has at least one ink carrier. A printing substance, such as ink is applied to the ink carrier and at least some of that ink is transferred to a substrate at a separation location. A light-hydraulic effect is used to accomplish this separation. Radiation energy that is transferred to the printing substance stimulates this transfer of the print substance to the substrate to be printed. The transport of the radiation energy takes place by the use of at least two energy beams of different wavelengths.

45 Claims, 2 Drawing Sheets

FOREIGN PATENT DOCUMENTS

| | | | |
|---|---|---|---|
| DE | 197 46 174 | C1 | 7/1999 |
| DE | 199 55 383 | A1 | 5/2001 |
| EP | 0 836 939 | B1 | 11/2001 |
| JP | 2002-86772 | | 3/2002 |
| WO | WO 01/72518 | A1 | 3/2001 |
| WO | WO 01/78985 | A1 | 3/2001 |

* cited by examiner

PRINTING MACHINES WITH AT LEAST ONE COLOR SUPPORT

CROSS-REFERENCE TO RELATED APPLICATIONS

This U.S. patent application is the U.S. national phase, under 35 USC 371, of PCT/DE2003/002907, filed Sep. 3, 2003; published as WO 2004/052648 A1 on Jun. 24, 2004 and claiming priority to DE 102 57 132.5, filed Dec. 6, 2002, the disclosures of which are expressly incorporated herein by reference.

FIELD OF THE INVENTION

The present invention is directed to printing presses with at least one ink carrier. A print substance is applied from the ink carrier to a material. This application takes place by making use of a light-hydraulic effect.

BACKGROUND OF THE INVENTION

A printing method, which is capable of using a print substance for printing with the aid of a preferably pulsed and focused energy beam, such as, for example, a laser beam or an electron beam, is known from WO 01/72518 A1. In this method the energy of the energy beam is introduced either directly or, following a conversion in an absorption layer, indirectly into the print substance. The print substance consists, for example, of a solvent, such as, for example color pigments dissolved in water. In both cases, a small gas bubble is explosively formed in the print substance by heat expansion or evaporation of, in particular, the solvent, as a result of the high energy density of the energy beams. This bubble, in the course of its exit from the print substance, displaces a portion of the print substance in the direction of a material to be imprinted, which material is located at a slight distance from the print substance, and sets a print point there. A so-called light-hydraulic effect is employed in this method, in which a shock wave is generated in a liquid by the light pulse. The light pulse is either directly introduced into the liquid, or acts indirectly on the liquid, and in both cases suddenly leads, in a point-like manner, to a thermally caused volume expansion in the liquid. The light-hydraulic effect is described in greater detail in EP 0 836 939 B1 while citing further sources.

In accordance with the above-mentioned WO 01/72518 A1, the print substance is applied as a homogeneous film to an ink carrier. The ink carrier is embodied, for example, as a rotating cylinder, and preferably is embodied as a transparent hollow cylinder which is made of glass. The ink carrier and the material to be imprinted are moved past each other without touching. If an absorption layer has been applied to the full surface of the ink carrier, the energy beam first penetrates the print substance, which, in this case, is not absorbent for its wavelength, and only then impacts on the absorption layer, which absorption layer converts the energy beam's radiation energy into heat or a pulse transfer. The absorption layer preferably consists of a crystalline material, preferably of poly-silicate. The crystal size of this material lies between 10 nm and 1000 nm and advantageously is less than the wavelength of the radiated energy employed. The thickness of the absorption layer is said to be less than 10 μm, and preferably is less than 1 μm. An energy beam directed to the print substance is said to have an incidence of more than 0° and less than 75°. The distance between the ink carrier and the material to be imprinted, which is moved past it at a conveying speed, is cited to be less than 2 mm, and preferably is even less than 0.5 mm. The pulse length of the energy radiation is said to be less than 1 μs, and is preferably between 100 ns and 200 ns. The output of the energy radiation lies at an order of magnitude of 50 W to 100 W or more. Laser diodes or arrays, i.e. arrangements thereof, are mentioned by way of example as energy sources. Specific information regarding the wavelength and the pulse sequence frequency of the energy radiation used is not present in this prior document.

An ink jet printer is known from DE 37 02 643 A1. Ink is applied in a thin layer of 10 μm to 100 μm to a glass substrate or to an ink ribbon, and points on the substrate or ribbon are heated, for a period of 0.1 μs to 1 μs, to more than 100° C. as a function of a beam of a laser, preferably a $CO_2$-laser, which beam has been modulated by use of an image signal. A bubble is formed which, when it bursts, transfers ink to a material to be imprinted, which material is moved past the glass substrate or the ink ribbon with the heated ink at a short distance of less than 1 mm. In a preferred embodiment, an ink jet printer for use in printing several printing inks, such as, for example, red, green, blue and black commercially available water-soluble ink is described, and wherein an ink cartridge is provided for each printing ink, each of which ink cartridges is sequentially introduced into the beam path of the laser. In connection with printing inks having little light-absorbing properties, such as red ink, or in particular yellow ink for example, a light-absorbing film of a layer thickness of less than 20 μm, which film has been evenly painted on the substrate, is employed, and on which film the light beam of the laser impinges. The light-absorbing film heats the ink which is in contact with it until a bubble is formed. The bubble is then driven out of the ink cartridge in the direction toward the material to be imprinted.

Since print substances of different colors, and therefore also of different material structures, are employed in printing technology, and wherein the print substances, which differ from each other, can be arranged, for example, on different ink carriers in the same printing press, it is desirable for different print substances to be printed by the same printing press in accordance with the printing processes described at the outset.

SUMMARY OF THE INVENTION

The object of the present invention is directed to providing printing presses with at least one ink carrier.

In accordance with the present invention, this object is attained by the provision of a printing press with at least one ink carrier. A print substance, that is to be transferred, at least in part, to a material to be printed, is applied to the ink carrier. Application of the print substance is accomplished by a light-hydraulic effect. Radiation energy is transported to the print substance and stimulates the transfer of the print substance to the material to be printed. At least one energy beam, and possibly additional energy beams provide the radiation energy.

Printing presses with at least one ink carrier are proposed in accordance with the present invention. A print substance is to be applied to the ink carrier. A transfer of at least a portion of the print substance to a material to be imprinted, which material is arranged spaced apart from the ink carrier, takes place by making use of a light-hydraulic effect. Radiation energy, which is transported to the print substance, stimulates the transfer of the print substance to the material to be imprinted. The printing press of the present invention is distinguished from prior devices in that the transport of the radiation energy takes place by the use of at least two energy beams of different wavelength.

The advantages to be obtained by the present invention consist, in particular, in that by using at least two energy beams, of different wavelength, for the transport of the radiation energy it can be assumed, with at least doubled probability, that it will be possible, by making use of the light-hydraulic effect, to stimulate print substances of different material structure and with different spectral behavior to accomplish at least a partial transfer of the print substances to the material to be imprinted. The wavelengths have been selected in an advantageous manner in such a way that a print substance customarily used in the printing press, such as, for example, a defined color, and which, because of its material structure and its spectral behavior, does not undergo the light-hydraulic effect at one of the defined wavelength, shows that effect in connection with the other available wavelength.

BRIEF DESCRIPTION OF THE DRAWINGS

Preferred embodiments of the present invention are represented in the drawings and will be described in greater detail in what follows.

Shown are in.

DESCRIPTION OF THE PREFERRED EMBODIMENT

Figure 1:
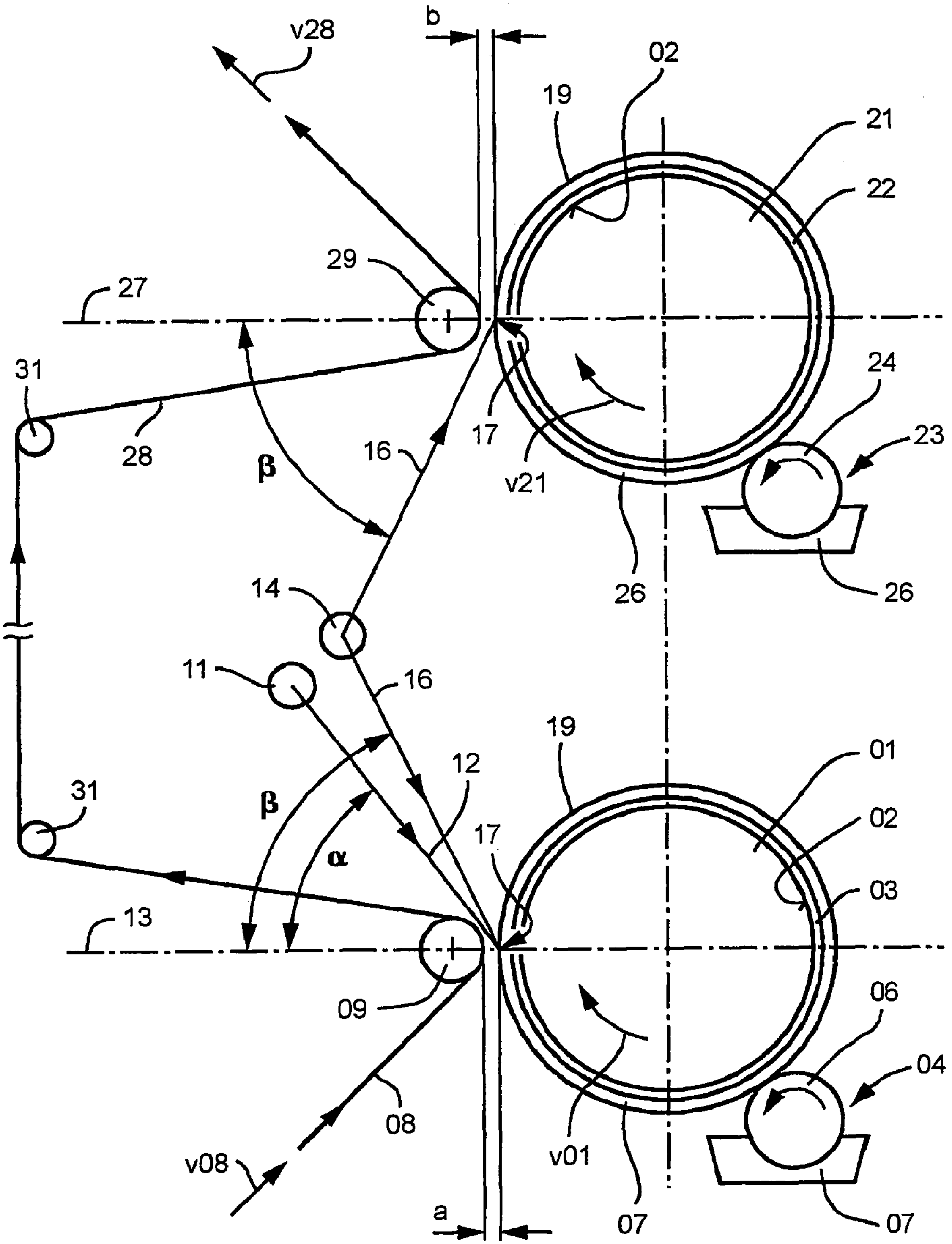
FIG. 1, a simplified representation of a printing group of a printing press in accordance with the present invention, and FIG. 2, an enlarged portion of FIG. 1 and representing the printing process of the present invention.

In a simplified representation, FIG. 1 shows a printing group of a printing press with at least one ink carrier 01, which is embodied, for example, as a first rotating cylinder 01. An absorption layer 03 has preferably been applied to a shell face 02 of the cylinder 01, preferably over the entire surface of shell face 02. The absorption layer 03 has a layer thickness of, for example, less than 20 μm, and in particular of less than 5 μm. This absorption layer 03 has been represented in FIGS. 1 and 2 at a substantially enlarged thickness for better visibility. By the use of at least one ink application roller 06, a first inking unit 04, which is assigned to the cylinder 01 applies, for example, a film of a first print substance 07, preferably over the entire surface of this cylinder 01. The film of the first print substance 07 is also represented with an enlarged thickness in FIGS. 1 and 2.

A first material 08 to be imprinted, such as, for example, a sheet 08 or a web 08 of material, and in particular a paper web 08, is arranged at a spacing distance "a" of preferably less than 2 mm, and in particular of less than 0.5 mm, in front of the first cylinder 01, or preferably is passed in front of the cylinder 01 at a transport speed v08, which transport speed v08 is preferably matched to a speed of rotation v01 of the cylinder 01. To arrange the material 08 to be imprinted in front of the first cylinder 01, a first deflection roller 09 or a first deflection cylinder 09 can be provided, extending parallel to the axial direction of the cylinder 01, and spaced radially therefrom, which deflection cylinder 09, for one, preferably stabilizes the material 08 to be imprinted in its position, i.e. in particular stabilizes material 08 in its distance "a" from the cylinder 01, and furthermore makes it possible to deflect the material 08 to be imprinted in its transport direction from the cylinder 01. The deflection cylinder 08 typically reroutes the material 08 to be imprinted into a direction which, in particular, is facing away from the cylinder 01.

A first radiation source 11 with a narrow beam divergence, which is thus a so-called spot light source, such as, for example, a laser 11, and in particular which is a solid state laser 11, such as, for example, a ruby laser or a neodymium-YAG laser, emits radiation energy of a high energy density in the form of a first energy beam 12 to the print substance 07 applied to the cylinder 01. The first energy beam 12 forms an angle α of more than 0° and of less than 90°, and preferably of less than 45°, with a line 13 which is normal to a surface 19 of the print substance 07 at the point of printing. At least one second radiation source 14, also with a narrow beam divergence, such as, for example, again a laser 14, and in particular a solid state laser 14, also emits radiation energy of high energy density in the form of a second energy beam 16, for example, to the print substance 07 that has been applied to the first cylinder 01. The second energy beam 16 also forms an angle β of more than 0° and of less than 90°, and preferably of less than 45°, with a line 13 which is normal to a surface 19 of the print substance 07 applied to the cylinder 01, at the point of printing or with a normal line 27 of a surface 19 of a second print substance 26. The arrangement of the first and second radiation sources 11, 14 can be selected in such a way that the angles α, β which are formed between the normal lines 13, 27 and the energy beams 12, 16 of the radiation sources 11 and 14 are at least approximately identical. The radiation sources 11, 14 can also be configured in such a way that spatially they constitute a single radiation source, for example, which single radiation source is capable of emitting at least two different energy beams 12, 16, wherein the two different energy beams 12, 16 have two wavelengths which differ from each other. For example, some laser systems can be selectively stimulated to emit two energy beams 12, 16 of different wavelengths. As an example, frequency-doubling or frequency-tripling neodymium-YAG lasers are examples of such laser systems, whose energy beams 12, 16 have half or a third of their natural wavelength of 1064 nm. Or the two radiation sources 11, 14 can result when a single radiation source 11, 14, such as, for example, a dye laser, in which preferably organic dyes, for example rhodamines, coumarines or oxazines, have been dissolved in a carrier medium, such as, for example, a carrier fluid, emits radiation energy within a spectral range of 60 nm or more, for example, out of which radiation energy at least two energy beams 12, 16 of different wavelengths can be separated, preferably by the use of optical devices, such as, for example, filters. Preferably the radiation sources 11, 14 emit their radiated energy in pulses of short length, such as, for example, of clearly less than 1 μm, and in particular of approximately 100 ns, and at a high pulse repetition frequency of, for example, 1 MHz or more.

Figure 2:
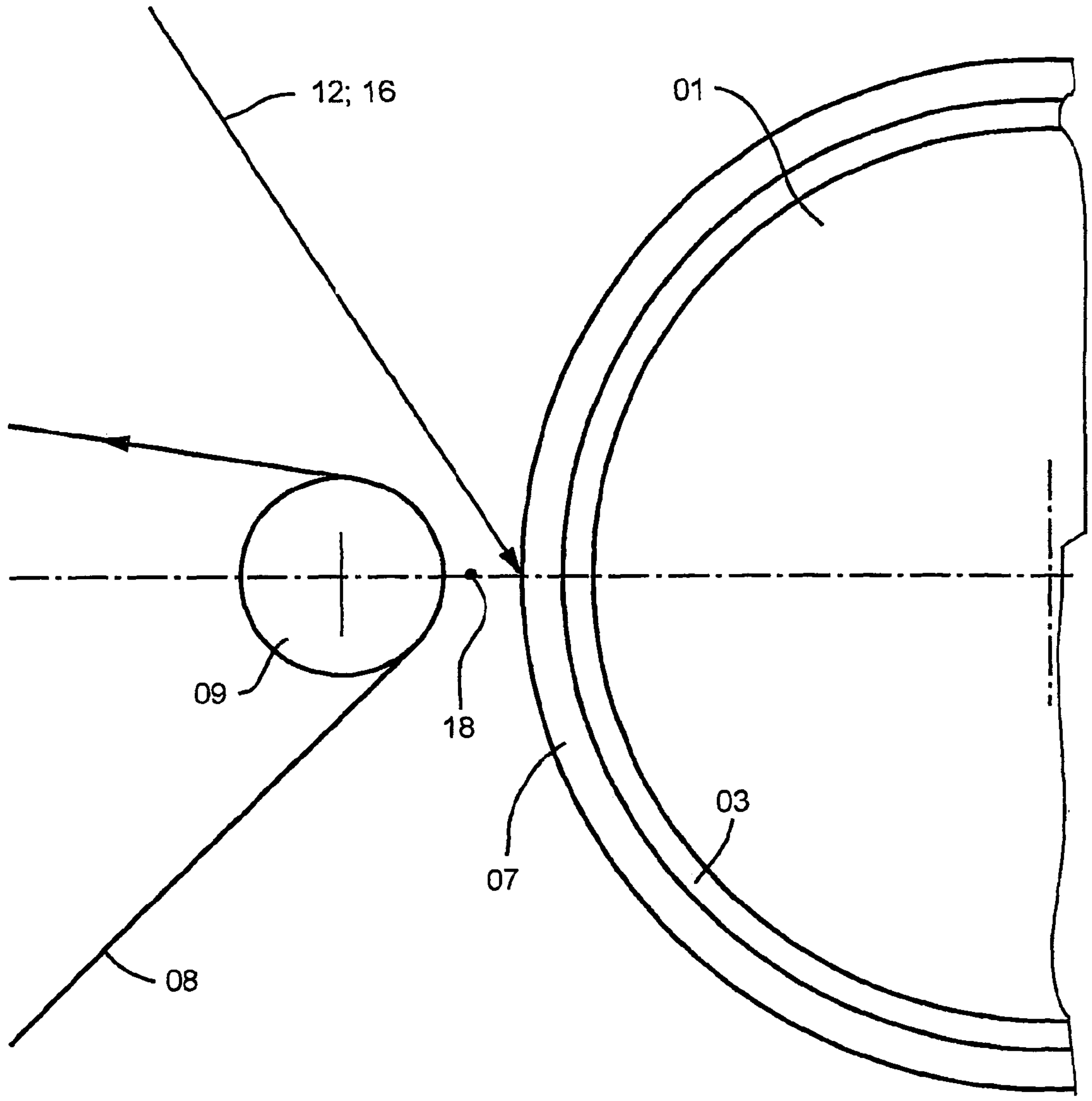

The absorption layer 03 applied to the ink carrier 01 absorbs the radiation energy emitted by the radiation sources 11, 14 and converts it to heat or to a pulse transfer. In accordance with the light-hydraulic effect, a gas bubble is explosively formed in the print substance 07 by heat expansion or evaporation, which gas bubble, in the course of its exit from the print substance 07, displaces a portion 18 of the print substance 07 in the direction toward the material 08 to be imprinted, which material 08 is spaced apart from the print substance. This displaced portion 18 of the print substance 07 sets a print point on the material 08 to be imprinted. FIG. 2, which represents an enlargement of a portion of FIG. 1, shows, by way of example how, as a result of the incidence of energy beams 12, 16 on the print substance 07, a portion 18 of the print substance 07, for example in the form of a drop 18 of the print substance 07, is released from the print substance 07 which was taken along on the surface of the cylinder 01. This drop 18 is transferred to the spaced-apart arranged material 08 to be imprinted.

At least one further, second ink carrier 21 can be provided in the printing press, as seen in FIG. 1. This second ink carrier 21 preferably is substantially identical to the previously described first ink carrier 01 in its structure and its use. Second ink carrier 21 is, for example, configured as a second rotating cylinder 21 with an absorption layer 22, for example. A second print substance 26 is applied to the surface of the second cylinder 21, preferably on the absorption layer 22, by operation of a second inking unit 23 with, for example, a second ink application roller 24 of the second inking unit 23 being assigned to the second cylinder 21. The first print substance 07 and the second print substance 26 preferably differ in their material structure or in their spectral behavior. Thus, the first and second print substances 07, 26 used can be embodied, such as, for example, two different printing inks, such as, for example, a colored ink and a black ink, which two printing inks 07, 26 have absorption capabilities of the energy beams 12, 16, that are available in the printing press which absorption capabilities differ from each other. As a rule, the first and second print substances 07, 26 are each a dispersion of a solid coloring agent, a liquid binder and, if required, an auxiliary printing medium, which is added to the print substance 07, 26 for achieving a special property of the print substance 07, 26. Such a special property may be, for example, its consistency, drying, abrasion resistance or luster, wherein the coloring agent consists, for example, of pulverulent pigments, which are finely dispersed in the binder which may be, for example, a viscous oily varnish.

A second material 28 to be imprinted, such as, for example, a sheet 28 or a web 28 of material, and in particular a paper web 28, is arranged at a distance "b" of preferably less than 2 mm, and in particular of less than 0.5 mm, in front of the second cylinder 21. The second material 28 may be passed in front of the cylinder 21 at a transport speed v28, which transport speed v28 is preferably matched to the rotation speed v21 of the cylinder 21. For use in arranging the second material 28 to be imprinted in front of the second cylinder 21, a second deflection roller 29 or deflection cylinder 29 can be provided spaced from cylinder 21 in a radial direction, and parallel in the axial direction of this cylinder 21. The second deflection roller 29 for one preferably stabilizes the material 28 to be imprinted in its position, particularly in its distance "b" from the second cylinder 21, and furthermore makes it possible to deflect the material 28 to be imprinted in its transport direction from the cylinder 21. This second deflection roller 29 reroutes the material 28 to be imprinted into a direction facing away from the cylinder 21 in particular. In a preferred embodiment of the present invention, the first material 08 to be imprinted and the second material 28 to be imprinted form a coherent web 08, 28 of material, which coherent web is conducted from the first cylinder 01 to the second cylinder 21 by the use of an arrangement of deflection rollers 31 or deflection cylinders 31, for example.

The printing press described hereinabove can be expanded, as required, in an appropriate manner by the provision of further ink carriers and of further radiation sources which expansion, however, has not been represented in the drawing figures for the purpose of maintaining clarity. The printing press can be rigged as a multi-color printing press in this way, which multi-color printing press is in a position to substantially simultaneously print the customary four base colors black, cyan, magenta and yellow, as well as further decorative colors and also special colors, if desired. These various print substances obviously differ in their material structure and in their spectral behavior.

The energy beams 12, 16, which are preferably energy beams 12, 16 of different wavelengths, can both be directed to the same, for example the first ink carrier 01. This option permits the printing of print substances 07 of, for example, the same color, but of different material structure, on the same print carrier 01. The difference in the material structure of the print substance 07 can be caused by, for example, different formulations of the print substances 07. An alternative arrangement, as shown in FIG. 1, provides that at least one energy beam 12, 16 is directed to another, second ink carrier 21, can at least be selectively directed there. It is also possible to provide arrangements wherein a first energy beam 12 of a first wavelength is, for example, directed to three ink carriers 01, 21, preferably to the two ink carriers 01 with colored ink, and, wherein in the course of the ongoing printing process, a second energy beam 16 of a second wavelength is directed, essentially at the same time, to the ink carrier 21 which is provided with the black ink. The wavelengths of the two energy sources 12, 16 preferably differ from each other.

A frequency-doubling neodymium-YAG laser, of a wavelength of 532 nm located in the green spectral range, could be directed to an ink carrier 01, 21 with a magenta-colored ink. A ruby laser, of a wavelength of 694 nm located in the cyan spectral range, could be directed to an ink carrier 01, 21 with a cyan-colored ink. A GaN semiconductor laser, of a wavelength of 395 nm to 440 nm located in the violet-blue spectral range, could be directed to an ink carrier 01, 21 with a yellow-colored ink. The absorption of the directed energy beam 12, 16 by the absorption layer 03 shows the highest effects on the print substance 07 if an energy beam 12, 16 of a wavelength is used which energy beam wavelength is complementary to the wavelength of the spectral range of the print substance 07, 26. In principle, energy beams 12, 16 of any arbitrary wavelength can be used for an ink carrier 01, 21 with black ink. However, a neodymium-YAG laser operated at its basic frequency and with a wavelength of 1064 nm located in the infrared range, is particularly well suited.

Accordingly, several parallel, activable radiation sources 11, 14 of different types or with energy beams 12, 16 of different wavelengths, can be provided for use with the same printing press. A solution thereby results regarding the radiation sources 11, 14 and possibly also their arrangement in the printing press. It is possible, in accordance with the specific printing requirements, to selectively employ the optimal radiation sources 11, 14, or the resultant energy beams 12, 16 with the optimum wavelength, pulse length, or amount of radiated energy for printing with the print substance 07, 26 for each ink carrier 01, 21 and for each print substance 07, 26. For example, it is possible, in accordance with the present invention, to provide four ink carriers 01, 21, and wherein one energy beam 12, 16 is directed on each one of the four ink carriers 01, 21, respectively, and wherein, with three ink carriers 01, 21, the respective energy beam 12, 16 impinges at the same angle β of preferably less than 45° on the surface 19 of the print substance 26 while, for example, the energy beam 12, which is directed on the fourth ink carrier 01, is aligned with the transmission direction of the print substance 07 to the material 08 to be imprinted. With an arrangement of the present invention, wherein each one of the four ink carriers 01, 21 is embodied as a cylinder, with three of the four ink carriers 01, 21 the energy beam 12, 16 can therefore be directed from the outside of the cylinder onto the cylinder. With the fourth ink carrier 01, the associated energy beam 12 is directed from the inside of the cylinder to the print substance 07. In connection with this fourth ink carrier 01, the radiation source 11 emitting the energy beam 12 can be arranged, for example, in the interior of the cylinder. Alternatively, the energy beam 12 is directed from the radiation source 12, which is arranged outside the cylinder, into the interior of the cylinder by the use of optical assemblies and is from there directed on the print substance 07, for example by the use of mirrors.

Advantageously, the energy beams 12, 16 are focused on an impact point 17 on a surface 19 of the print substance 07, 26 applied to the ink carriers 01, 21, which surface 19 faces the material 08 to be imprinted. A focus of the energy beam 12, 16, at the impact point 17, has a diameter of less than 30 μm, and preferably of less than 20 μm. Optical devices or the like, such as, for example, a polygonal mirror, which is not represented in the drawing figures, can be provided, which optical devices deflect the energy beams 12, 16, preferably in the axial direction of the ink carriers 01, 21. Line-by-line imprinting of the materials 08, 28 to be imprinted thus can take place by the deflection of the energy beams 12, 16.

The radiation sources 11, 14 are preferably arranged fixed in place with respect to the printing press. The peripheral units of the laser systems, such as, for example, the devices required for their energy supply or cooling, are preferably arranged outside of the printing press. However, they can also be arranged in the interior of a cylinder that is embodied as an ink carrier 01, 21. Alternatively, the energy beam 12, 16 from the radiation sources 11, 14 can be conducted by optical elements into the interior of the ink carrier 01, 21, which is embodied as a cylinder, in order to be directed from there to the print substance 07, 26. The beam path of the energy beams 12, 16 emitted by the radiation sources 11, 14 can be changeable. For example, the beam path can be conducted, by optical guide systems or by rerouting systems, to different locations of the printing press, and in particular to different ink carriers 01, 21.

While preferred embodiments of printing machines with at least one color support, in accordance with the present invention, have been set forth fully and completely hereinabove, it will be apparent to one of skill in the art that various changes in, for example the drives for the ink carriers and the material webs, the specific structures of the inking units, and the like could be made without departing from the true spirit and scope of the present invention which is accordingly to be limited only by the appended claims.

What is claimed is:

1. A printing press adapted to print a material to be imprinted comprising:

at least a first ink carrier, said at least first ink carrier being spaced at a first distance from the material to be imprinted;

a print substance selected from a group of print substances having different material structure and applied to said at least first ink carrier; and at least first and second energy beams of first and second different wavelengths, each of said at least first and second energy beams being selectable to selectively transport radiation energy to said selected print substance on said at least first ink carrier, a transfer of at least a portion of said selected print substance from said at least first ink carrier to the material to be printed in response to a light-hydraulic effort stimulated in said selected print substance applied to said at least first ink carrier by said radiation energy transported to said selected print substance on said at least first ink carrier by said selected one of said at least first and second energy beams, each of whose selected wavelength stimulates a different one of said group of said print substances selectively applied to said at least first ink carrier.

2. The printing press of claim 1 further including at least a second ink carrier spaced at a second distance from the material to be printed, a second print substance applied to said second print carrier and wherein at least one of said at least first and second energy beams is directed at each of said first and second ink carriers.

3. The printing press of claim 2 wherein each of said at least first and second ink carriers supports a different print substance.

4. The printing press of claim 3 wherein said energy beam directed to each of said first and second ink carriers is selected having a wavelength adapted to stimulate said print substance applied to said ink carrier to which said energy beam is directed.

5. The printing press of claim 3 wherein said different print substances have one of said different material structure and spectral behavior.

6. The printing press of claim 3 further including selectively different radiation sources for said at least first and second energy beams of said first and second wavelengths which are used for said different print substances. directed.

7. The printing press of claim 3 wherein said at least first and second print substances include a colored ink and a black ink and further wherein different ones of said at least first and second energy beams are employed with said colored ink and said black ink.

8. The printing press of claim 2 wherein at least said first and second energy beams of said first and second wavelength are both directed on one of said at least first and second ink carriers.

9. The printing press of claim 8 wherein said energy beam directed to each said ink carrier is selected having a wavelength adapted to stimulate said print substance applied to said ink carrier to which said energy beam is directed.

10. The printing press of claim 2 wherein one of said at least first and second energy beams is directed toward one of said first and second ink carriers in a direction aligned with a transfer direction of said print substance on said one of said ink carriers to the material to be printed and wherein another one of said at least first and second energy beams is directed on another of said at least first and second ink carriers at an angle formed with a line normal to a surface of said print substance on said another of said first and second ink carriers.

11. The printing press of claim 10 wherein each said angle is greater than 0° and is less than 90°.

12. The printing press of claim 11 wherein said angle is greater than 0° and is less than 45°.

13. The printing press of claim 10 wherein angles of two different ones of said at least first and second energy beams are the same.

14. The printing press of claim 2 wherein said radiation energy simultaneously transported to said at least first and second ink carriers stimulates the transfer of respective ones of said different print substances from said ink carriers to the same material to be supported.

15. The printing press of claim 2 wherein said at least one energy beam is directed on each of said at least first and second ink carriers.

16. The printing press of claim 2 wherein the material to be imprinted includes a first material arranged at a first distance from said at least first ink carrier and a second material arranged at a second distance from said second ink carrier.

17. The printing press of claim 16 wherein said first and second distances are each less than 2 mm.

18. The printing press of claim 17 wherein said first and second distances are each less than 0.5 mm.

19. The printing press of claim 16 wherein said first material to be imprinted and said second material to be imprinted constitute a coherent web of material.

20. The printing press of claim 2 wherein one of said at least first and second energy beams directed to one of said at least first and second ink carriers is aligned with a transfer direction of said print substance to the material to be imprinted and further wherein another of said at least first and second energy beams directed to another of said at least first and second ink carriers impinges on a surface of said print substance at an angle formed with a normal line of a surface of the print substance.

21. The printing press of claim 2 wherein one of said at least first and second energy beams can be selectively directed on different ones of said at least first and second ink carriers.

22. The printing press of claim 1 wherein each of said at least first and second energy beams forms a shock wave in said print substance and further wherein said shock wave drives a portion of said print substance out of said print substance.

23. The printing press of claim 1 wherein said at least first and second energy beams are each emitted by a radiation source.

24. The printing press of claim 1 further including a single radiation source which emits said radiation energy from which said at least first and second energy beams of different wavelengths can be separated.

25. The printing press of claim 1 further including at least two radiation sources each of which emits one of said energy beams of different wavelengths.

26. The printing press of claim 1 further including a radiation source which selectively emits each of said at least two energy beams of different wavelengths.

27. The printing press of claim 1 further including a radiation source for said at least first and second energy beams, said radiation source being a laser.

28. The printing press of claim 1 wherein said at least first and second energy beams consist of pulses of a duration of less than 1 μm.

29. The printing press of claim 1 wherein said at least first and second energy beams consist of pulses with a pulse repetition frequency of at least 1 MHz.

30. The printing press of claim 1 further including a radiation source fixed in place with respect to said printing press and further including an optical guide system, said at least first and second energy beams being directed from said radiation source to different locations of the printing press by said optical guide system.

31. The printing press of claim 30 wherein one of said at least first and second energy beams is directed on said at least one ink carrier aligned with a transfer direction of said at least first print substrate to the material to be printed.

32. The printing press of claim 1 wherein at least one of said at least first and second energy beams impinges on a surface of said print substance at an angle formed with a normal line of a surface of the print substance.

33. The printing press of claim 32 wherein said angle is greater than 0° and is less than 90°.

34. The printing press of claim 33 wherein said angle is greater than 0° and is less than 45°.

35. The printing press of claim 32 wherein angles of two different ones of said at least first and second energy beams are the same.

36. The printing press of claim 1 further including an absorption layer applied to said at least first ink carrier.

37. The printing press of claim 36 wherein said absorption layer has been applied to an entire surface of said at least one ink carrier.

38. The printing press of claim 1 wherein said at least first ink carrier is a rotating cylinder.

39. The printing press of claim 1 wherein the material to be imprinted is a paper web.

40. The printing press of claim 1 wherein the material to be imprinted is a sheet.

41. The printing press of claim 1 wherein the material to be imprinted passes by said at least first ink carrier at a transport speed.

42. The printing press of claim 1 wherein said at least first ink carrier is a cylinder having a rotation speed and further wherein the material to be imprinted has a transport speed matched to said rotation speed.

43. The printing press of claim 1 further including a deflection roller located spaced from said at least first ink carrier.

44. The printing press of claim 43 wherein said deflection roller is adapted to stabilize said first distance between said at least first ink carrier and the material to be imprinted.

45. The printing press of claim 43 wherein said deflection roller guides the material to be printed in a transport direction facing away from said at least first ink carrier.

* * * * *